United States Patent
Broman et al.

(10) Patent No.: US 9,526,530 B2
(45) Date of Patent: Dec. 27, 2016

(54) ARTHOPLASTY REVISION SYSTEM AND METHOD

(71) Applicant: GLOBUS MEDICAL, INC., Audubon, PA (US)

(72) Inventors: Richard J. Broman, Kirkland, WA (US); Thomas Mcleer, Redmond, WA (US); Leonard Tokish, Jr., Redmond, WA (US); Mark A. Reiley, Oakland, CA (US); Sean S. Suh, Jamesburg, NJ (US)

(73) Assignee: GLOBUS MEDICAL, INC., Audubon, PA (US)

( * ) Notice: Subject to any disclaimer, the term of this patent is extended or adjusted under 35 U.S.C. 154(b) by 1 day.

(21) Appl. No.: 14/619,574

(22) Filed: Feb. 11, 2015

(65) Prior Publication Data

US 2015/0150603 A1 Jun. 4, 2015

Related U.S. Application Data

(63) Continuation of application No. 13/033,082, filed on Feb. 23, 2011, now Pat. No. 8,979,907, which is a
(Continued)

(51) Int. Cl.
*A61B 17/70* (2006.01)
*A61F 2/44* (2006.01)
*A61F 2/30* (2006.01)

(52) U.S. Cl.
CPC ....... *A61B 17/7049* (2013.01); *A61B 17/7011* (2013.01); *A61B 17/7041* (2013.01);
(Continued)

(58) Field of Classification Search
CPC ............. A61B 17/7011; A61B 17/7041; A61B 17/7049; A61F 2/4405; A61F 2/4455; A61F 2220/0033; A61F 2220/0025; A61F 2002/30367; A61F 2002/30507; A61F 2002/3069
(Continued)

(56) References Cited

U.S. PATENT DOCUMENTS 5,487,742 A * 1/1996 Cotrel ................ A61B 17/7052
606/250
5,601,552 A * 2/1997 Cotrel ................ A61B 17/7049
24/135 N
(Continued)

*Primary Examiner* — Pedro Philogene

(57) ABSTRACT

The present method includes the following steps: removing a portion of a previously implanted spinal arthroplasty device; and attaching a revision component to a remaining portion of the previously implanted spinal arthroplasty device to alter a biomechanical characteristic of the implanted arthroplasty device. Another aspect of the invention provides a method of limiting motion between adjacent vertebrae including the steps of accessing an implanted spinal arthroplasty device comprising a cephalad component fixed to a first vertebra and a caudal component fixed to a second vertebra inferior to the first vertebra, the cephalad and caudal components having a range of motion between them, and attaching a revision component to the cephalad and caudal components to reduce the range of motion. The invention also includes revision devices for revising the biomechanics of implanted spinal arthroplasty devices.

20 Claims, 13 Drawing Sheets

Related U.S. Application Data continuation of application No. 11/642,417, filed on Dec. 20, 2006, now Pat. No. 7,914,556, which is a continuation-in-part of application No. 11/206,676, filed on Aug. 17, 2005, now abandoned, which is a continuation-in-part of application No. 11/071,541, filed on Mar. 2, 2005, now Pat. No. 7,674,293.

(60) Provisional application No. 60/752,277, filed on Dec. 20, 2005, provisional application No. 60/847,013, filed on Sep. 25, 2006.

(52) U.S. Cl.
CPC .......... *A61F 2/4405* (2013.01); *A61F 2/4455* (2013.01); *A61F 2002/3069* (2013.01); *A61F 2002/30367* (2013.01); *A61F 2002/30507* (2013.01); *A61F 2220/0025* (2013.01); *A61F 2220/0033* (2013.01)

(58) Field of Classification Search
USPC .... 606/246–279, 301–308; 623/17.11–17.16
See application file for complete search history.

(56) References Cited

U.S. PATENT DOCUMENTS

| | | | |
|---|---|---|---|
| 7,691,145 B2 * | 4/2010 | Reiley | A61B 17/1671 606/247 |
| 8,226,689 B2 * | 7/2012 | Jones | A61B 17/7049 606/250 |
| 2006/0052785 A1 * | 3/2006 | Augostino | A61B 17/7049 606/247 |
| 2008/0200953 A1 * | 8/2008 | Reiley | A61B 17/1671 606/247 |

* cited by examiner

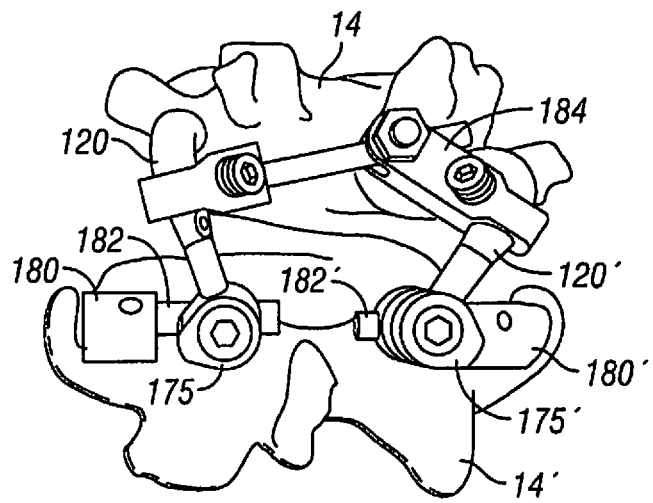
FIG. 2
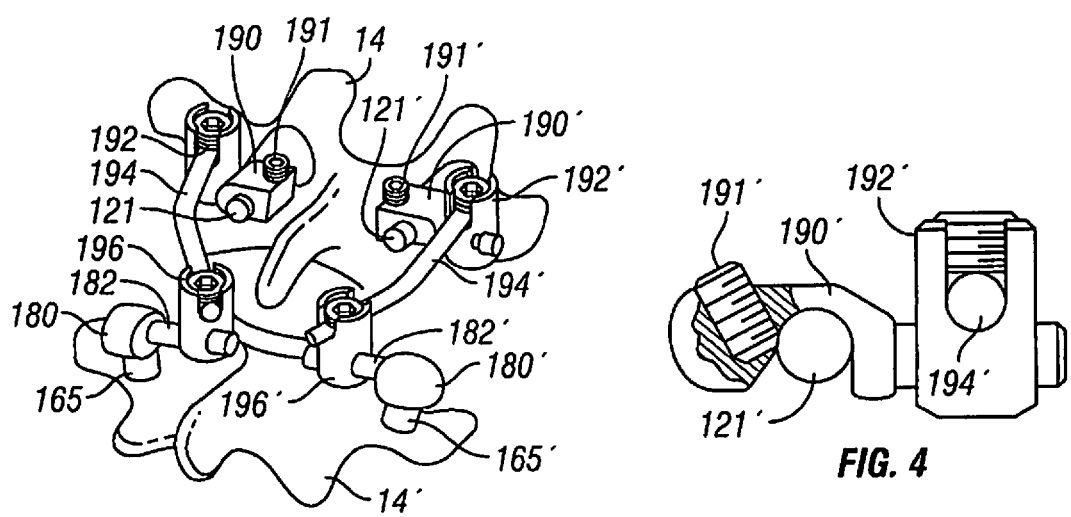
FIG. 3
FIG. 4

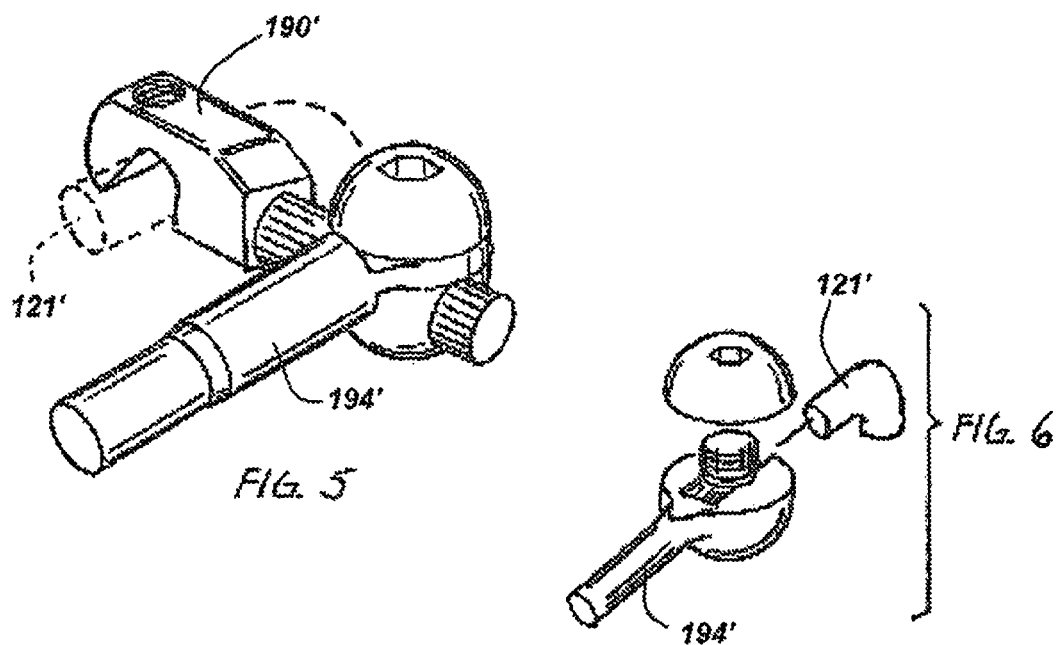
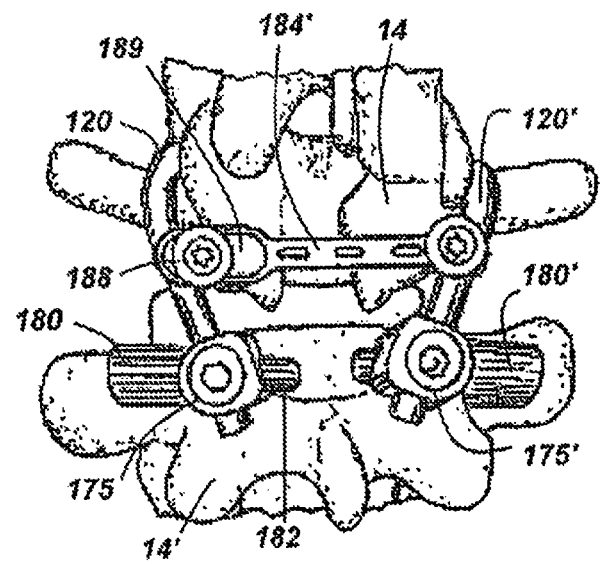

ARTHOPLASTY REVISION SYSTEM AND METHOD

CROSS-REFERENCE TO RELATED APPLICATIONS

The present application is a continuation of U.S. patent application Ser. No. 13/033,082, filed Feb. 23, 2011, which is a continuation application of U.S. patent application Ser. No. 11/642,417, filed Dec. 20, 2006, now issued as U.S. Pat. No. 7,914,556, which is a continuation-in-part of commonly assigned U.S. patent application Ser. No. 11/206,676, filed Aug. 17, 2005, which is a continuation-in-part of commonly assigned U.S. patent application Ser. No. 11/071,541, filed Mar. 2, 2005, now issued as U.S. Pat. No. 7,674,293. U.S. patent application Ser. No. 11/642,417 claims the benefit of U.S. Provisional Application 60/752,277, filed Dec. 20, 2005 and U.S. Provisional Application 60/847,013, filed Sep. 25, 2005. All of the references cited herein are hereby incorporated by reference in their entireties.

INCORPORATION BY REFERENCE

All publications and patent applications mentioned in this specification are herein incorporated by reference to the same extent as if each individual publication or patent application was specifically and individually indicated to be incorporated by reference.

FIELD OF THE INVENTION

The present invention generally relates to devices and surgical methods for treatment of various spinal pathologies. More specifically, the present invention is directed to configurable and anatomically adaptable implantable devices for use in a spine and surgical procedures for altering the biomechanics of a spine, either temporarily or permanently. The devices alter, replace and/or revise existing anatomy and/or previously implanted devices.

BACKGROUND OF THE INVENTION

Back pain, particularly in the small of the back, or lumbosacral region (L4-S1) of the spine, is a common ailment. In many cases, the pain severely limits a person's functional ability and quality of life. Back pain interferes with work, routine daily activities, and recreation. It is estimated that Americans spend $50 billion each year on low back pain alone. It is the most common cause of job-related disability and a leading contributor to missed work.

Through disease or injury, the laminae, spinous process, articular processes, facets and/or facet capsules of one or more vertebral bodies along with one or more intervertebral discs can become damaged, which can result in a loss of proper alignment or loss of proper articulation of the vertebra. This damage can also result in an anatomical change, loss of mobility, and pain or discomfort. For example, the vertebral facet joints can be damaged by traumatic injury or as a result of disease. Diseases damaging the spine and/or facets include osteoarthritis where the cartilage of joints is gradually worn away and the adjacent bone is remodeled, ankylosing spondylolysis (or rheumatoid arthritis) of the spine which can lead to spinal rigidity, and degenerative spondylolisthesis which results in a forward displacement of the lumbar vertebra on the sacrum. Damage to facet joints of the vertebral body often results in pressure on nerves, commonly referred to as "pinched" nerves, or nerve compression or impingement. The result is pain, misaligned anatomy, a change in biomechanics and a corresponding loss of mobility. Pressure on nerves can also occur without facet joint pathology, e.g., as a result of a herniated disc.

One conventional treatment of facet joint pathology is spine stabilization, also known as intervertebral stabilization. Intervertebral stabilization desirably controls, prevents or limits relative motion between the vertebrae through the use of spinal hardware, removal of some or all of the intervertebral disc, fixation of the facet joints, bone graft/ osteo-inductive/osteo-conductive material positioned between the vertebral bodies (with or without concurrent insertion of fusion cages), and/or some combination thereof, resulting in the fixation of (or limiting the motion of) any number of adjacent vertebrae to stabilize and prevent/limit/ control relative movement between those treated vertebrae.

Although spine fusion surgery is an efficacious treatment, complications can nonetheless result. Patients undergoing spine surgery frequently continue to experience symptoms. For surgical procedures in the lumbar spine, failure rates as high as 37% have been reported after lumbar fusion and 30% for surgery without fusion. See Eichholz, et al., "Complications of Revision Spinal Surgery," Neurosurg Focus 15(3): 1-4 (2003). Post-operative problems can include decompression related problems, and fusion related problems. Decompression related problems (i.e., loss of normal spine balance resulting in the head and trunk no longer being centered over the pelvis) include, for example, recurrent disc herniation, spinal stenosis, chronic nerve injury, infection, and decompression. Fusion related problems can include, pain from the bone harvest site, failure of a fusion to develop, loosening of the implanted devices, nerve irritation caused by the devices, infection, and poor alignment of the spine.

Stabilization of vertebral bodies can also be achieved (to varying degrees) from a wide variety of procedures, including the insertion of motion limiting devices (such as intervertebral spacers, artificial ligaments and/or dynamic stabilization devices), devices promoting arthrodesis (rod and screw systems, cables, fusion cages, etc.), and complete removal of some or all of a vertebral body from the spinal column (which may be due to extensive bone damage and/or tumorous growth inside the bone) and insertion of a vertebral body replacement (generally anchored into the adjacent upper and lower vertebral bodies). Various devices are known for fixing the spine and/or sacral bone adjacent the vertebra, as well as attaching devices used for fixation, including devices disclosed in: U.S. Pat. Nos. 6,585,769; 6,290,703; 5,782,833; 5,738,585; 6,547,790; 6,638,321; 6,520,963; 6,074,391; 5,569,247; 5,891,145; 6,090,111; 6,451,021; 5,683,392; 5,863,293; 5,964,760; 6,010,503; 6,019,759; 6,540,749; 6,077,262; 6,248,105; 6,524,315; 5,797,911; 5,879,350; 5,885,285; 5,643,263; 6,565,565; 5,725,527; 6,471,705; 6,554,843; 5,575,792; 5,688,274; 5,690,630; 6,022,350; 4,805,602; 5,474,555; 4,611,581; 5,129,900; 5,741,255; 6,132,430; and U.S. Patent Publication No. 2002/0120272.

More recently, various treatments have been proposed and developed as alternatives to spinal fusion. Many of these treatments seek to restore (and/or maintain) some, or all, of the natural motion of the treated spinal unit, and can include intervertebral disc replacement, nucleus replacement, facet joint resurfacing, and facet joint replacement. Such solutions typically include devices that do not substantially impair spinal movement. See, U.S. Pat. Nos. 6,610,091; 6,811,567; 6,902,580; 5,571,171; and Re 36,758; and PCT Publication Nos. WO 01/158563, WO 2004/103228, WO 2005/009301, and WO 2004/103227. Thus, spinal arthroplasty has become an acceptable alternative to fusion, particularly in cases of degenerative disc disease. Arthroplasty devices can be particularly useful because the devices are designed to create an artificial joint or restore the functional integrity and power of a joint

SUMMARY OF THE INVENTION

It may be necessary to alter or revise an implanted spinal prosthesis or fusion device. For example, due to the continued progress of spine disease, a spine surgeon may need to remove part or all of a previously implanted arthroplasty device in order to provide access to the patient's vertebra(e) and/or disc. After performing a surgical procedure on the patient (e.g., implantation of an artificial disc, resection of the lamina, etc.), the surgeon may want to provide the patient with a prosthesis to replace the function of the original device or to perform an entirely new function. It would be desirable to use a remaining portion of the implanted arthroplasty device as part of the new prosthesis.

In another example, even if no portion of an implanted device is removed, it may be desirable to revise the biomechanical function of the implanted device. For example, an implanted arthroplasty device may permit movement between the adjacent vertebrae to which it is attached. It may be desirable to change, limit or completely eliminate the motion between the cephalad and caudal portions of the prosthesis, thereby changing, limiting or eliminating movement between the vertebrae, without removal, or with only partial removal, of the existing implant. It would therefore be desirable to add a revision device to the arthroplasty implant to change the implant's biomechanics.

One aspect of the invention provides a method of revising an implanted arthroplasty device, such as an implanted arthroplasty device having a cephalad component fixed to a first vertebra and a caudal component fixed to a second vertebra inferior to the first vertebra. The method includes the following steps: removing a portion of a previously implanted spinal arthroplasty device; and attaching a revision component to a remaining portion of the previously implanted spinal arthroplasty device to alter a biomechanical characteristic of the implanted arthroplasty device. In some embodiments, wherein the caudal component includes a caudal cup, the removing step includes the step of removing the caudal cup from a fixation element. The attaching step may also include the step of attaching an attachment device to the caudal cup fixation element.

In some embodiments, wherein the cephalad component includes a cephalad arm and a cephalad bearing element, the removing step includes the step of removing the cephalad bearing element from the cephalad arm. The attaching step may also include the step of attaching a connector housing to the cephalad arm and attaching the connector housing to an other arthroplasty element (such as the caudal component) or revision component. The removing step may also include the step of removing a caudal cup from a caudal fixation element, with the attaching step including the step of attaching a caudal attachment device to the caudal fixation element and attaching the housing to the caudal attachment device. In situations in which the cephalad component has two cephalad arms, the attaching step may include the step of attaching a crossbar to the two cephalad arms.

In embodiments in which the cephalad component has an implanted cephalad arm, the removing step may include the step of removing a portion of the implanted cephalad arm. The attaching step may also include the step of attaching a new cephalad arm to a remaining portion of the implanted cephalad arm, such as by attaching a connector housing to the new cephalad arm and attaching the connector housing to an other arthroplasty device element (such as the caudal component) or a revision component. The new cephalad arm may be located medial to or lateral to the implanted cephalad arm. The removing step further may also include the step of removing a caudal cup from a caudal fixation element, with the attaching step including the step of attaching a caudal attachment device to the caudal fixation element and attaching the housing to the caudal attachment device. In situations in which the cephalad component has two implanted cephalad arms, the removing step may include the step of removing a portion of each implanted cephalad arm and the attaching step may includes the steps of attaching a new cephalad arm to a remaining portion of each implanted cephalad arm and attaching a crossbar to the two new cephalad arms.

Another aspect of the invention provides a method of altering the biomechanics between first and second vertebrae including the steps of accessing an implanted spinal device (such as, e.g., a spinal arthroplasty device, a facet joint replacement device, a dynamic stabilization device, in interspinous space, and/or an artificial disc) comprising a cephalad component fixed to the first vertebra and a caudal component fixed to the second vertebra inferior to the first vertebra, the cephalad and caudal components having a biomechanical relationship (such as, e.g., a range of motion) between them, and attaching a revision component to the cephalad and caudal components to alter the biomechanical relationship (e.g., by reducing the range of motion). In some embodiments, the attaching step substantially eliminates motion between the cephalad and caudal components. In embodiments in which the cephalad component has a cephalad bearing element and the caudal component has a caudal bearing element, the attaching step may include the step of attaching a revision component extending from one side of the cephalad bearing element to an opposing side of the caudal bearing element. In embodiments in which the cephalad component further includes a cephalad arm, the attaching step may also include the step of attaching the revision component to the cephalad arm.

Yet another aspect of the invention provides a revision device for an implanted spinal arthroplasty device, where the implanted spinal arthroplasty device has a cephalad component fixed to a first vertebra and a caudal component fixed to a second vertebra inferior to the first vertebra. The revision device according to this aspect of the invention has an attachment component adapted to attach to a remaining portion of an arthroplasty device component after a portion of the arthroplasty device has been removed to alter a biomechanical characteristic of the arthroplasty device. In some embodiments in which the caudal component of the implanted arthroplasty device has a caudal cup, the revision device has a caudal attachment device adapted to be attached to a caudal cup fixation element after the caudal cup has been removed.

In embodiments in which the cephalad component of the implanted arthroplasty device has a cephalad arm, the revision device may have a connector housing adapted to be attached to the cephalad arm and to an other arthroplasty device element (such as the caudal component) or a revision component. In some embodiments, the revision device also includes a caudal attachment device adapted to be attached to a caudal cup fixation element after the caudal cup has been removed, the connector housing being adapted to be attached to the caudal attachment device. In some embodiments, the revision device has a cross-bar adapted to attach to two cephalad arms of the implanted spinal arthroplasty device.

In embodiments in which the implanted spinal arthroplasty device has a cephalad arm, the revision device may also include a new cephalad arm and an attachment mechanism adapted to attach the new cephalad arm to a remaining portion of the implanted cephalad arm (medially or laterally of the implanted cephalad arm) after a portion of the implanted cephalad arm has been removed. In such embodiments, the revision device may also have a connector housing attached to the new cephalad arm and being adapted to attach to an other arthroplasty device element (such as the caudal component) or revision device element. The revision device may also have a caudal attachment device adapted to be attached to a caudal cup fixation element after the caudal cup has been removed, the connector housing being adapted to be attached to the caudal attachment device. In embodiments in which the implanted spinal arthroplasty device has two cephalad arms, the revision device may have two new cephalad arms, each having an attachment mechanism adapted to attach one of the new cephalad arms to a remaining portion of a respective implanted cephalad arm after a portion of such implanted cephalad arm has been removed.

Still another aspect of the invention provides a revision device for an implanted spinal device (such as, e.g., a spinal arthroplasty device, a facet joint replacement device, a dynamic stabilization device, in interspinous space, and/or an artificial disc), where the implanted spinal arthroplasty device has a cephalad component fixed to a first vertebra and a caudal component fixed to a second vertebra inferior to the first vertebra, the cephalad and caudal components having a biomechanical relationship (such as, e.g., a range of motion) between them. The revision device according to this aspect of the invention includes a first surface adapted to interact with the cephalad component and a second surface adapted to interact with the caudal component to alter the biomechanical relationship (e.g., to limit motion) between the cephalad and caudal components. In some embodiments in which the cephalad component of the implanted spinal device has a cephalad bearing element and the caudal component has a caudal bearing element, the revision device is adapted to attach to the cephalad component on one side of the cephalad bearing element and to attach to the caudal component on a side of the caudal bearing element opposite to said one side to, e.g., limit or eliminate motion between the cephalad and caudal components. In embodiments in which the cephalad component also has a cephalad arm, the revision device may include an attachment mechanism adapted to attach to the cephalad arm.

Various other alternative aspects of the invention provide for the use of one or more revision devices for implanted spinal devices, such as spinal arthroplasty devices, motion limiting devices (such as intervertebral spacers, artificial ligaments and/or dynamic stabilization devices), devices promoting arthrodesis (rod and screw systems, cables, fusion cages, etc.), and/or vertebral replacement devices. The revision devices according to these aspects of the invention may include a linkage or linkages that serves to augment and/or replace a pre-existing connection between adjacent and/or non-adjacent vertebral bodies. Such devices can increase, decrease and/or alter the amount, range and/or quality of motion allowed or permitted between the targeted vertebral bodies, depending upon the desired surgical outcome, as well as the current condition and/or needs of the patient

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 2 shows an implanted spinal arthroplasty device that has been revised by a revision device according to on embodiment of the invention.

FIG. 3 shows an implanted spinal arthroplasty device that has been revised by a revision device according to another embodiment of the invention.

FIG. 4 shows details of one aspect of the embodiment of FIG. 3.

FIG. 5 shows details of an alternative connection mechanism to be used with the embodiment of FIG. 3.

FIG. 6 is an exploded view of yet another connection mechanism to be used with the embodiment of FIG. 3.

FIG. 7 shows an implanted spinal arthroplasty device that has been revised by a revision device according to yet another embodiment of the invention.

DETAILED DESCRIPTION OF THE INVENTION

Figure 1:
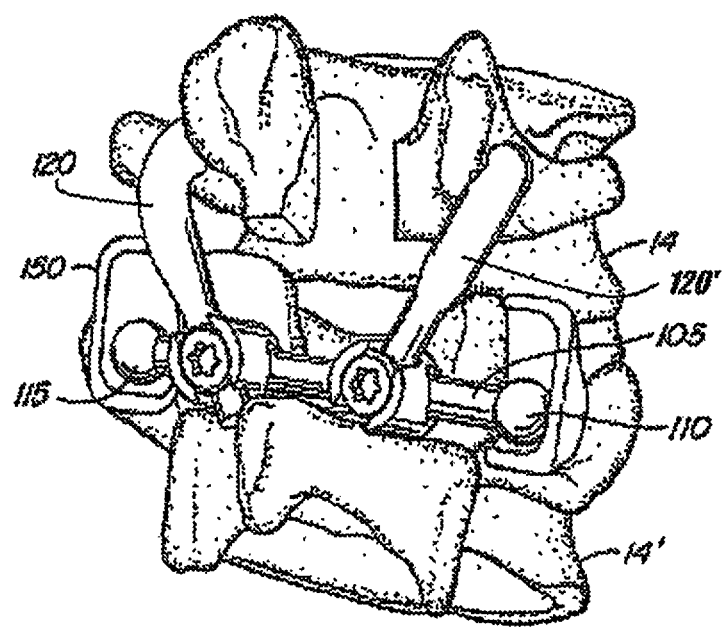
FIG. 1 is a perspective view of an implanted spinal arthroplasty device.

The revision devices and methods of this invention may be used with a variety of spinal implants, such as arthroplasty implants. FIG. 1 shows an exemplary spinal arthroplasty device attached to adjacent vertebrae 14 and 14'. The spinal arthroplasty device includes a crossbar 105, a pair of cephalad arms 120, 120' and a pair of caudal cups 150, 150'. Heads 110 and 115 at opposing ends of crossbar 105 interact with bearing surfaces inside caudal cups 150 and 150' to replace the articulating action of the patient's natural facet joints, which have been removed, when the patient flexes and extends his or her back. In this example, each cephalad arm 120, 120' attaches to the pedicle of the superior vertebra 14 as shown, via, e.g., a stem (not shown) inserted into the pedicle. The other ends of the cephalad arms attach to crossbar 105 via crossbar mounts 175 and 175'. The caudal cups 150 and 150' attach to the inferior vertebra 14' via, e.g., stems (not shown) inserted into the pedicles. Further details of this exemplary spinal arthroplasty device may be found in U.S. Ser. No. 11/206,676.

FIG. 2 shows an implanted spinal arthroplasty device that has been revised by a revision device. In this example, the revision device alters the biomechanics of the implanted device by substantially eliminating movement between the cephalad and caudal members and, thereby, between the adjacent vertebrae. The caudal cups that had been attached to inferior vertebra 14' have been removed from their stems, which remain implanted. The caudal cups may be removed, e.g., by grasping them with a grasping tool and/or through the application of energy (heat, vibration, ultrasound, etc.). In place of the caudal cups, attachment devices 180 and 180' are attached to the exposed portions of the caudal stems. Caudal attachment devices, such as rods 182 and 182', extend medially from attachment devices 180 and 180'. Alternatively, a single rod extending between attachment devices 180 and 180' may be used in place of shorter rods 182 and 182'.

As shown in FIG. 2, instead of attaching to a movable crossbar, cephalad arms 120 and 120' are now attached to the immovable caudal attachment devices via mounts 175 and 175' or other connectors or housings. Addition of the revision device therefore substantially eliminates movement between the remaining cephalad and caudal components of the implanted arthroplasty device and between vertebrae 14 and 14'. A crossbar 184 may be added between the cephalad arms for additional stability. The crossbar may have an adjustable length, as shown. Alternatively, the crossbar may have a fixed length and may possibly provide multiple cephalad arm attachment points selectable along its length, as shown, e.g., in FIG. 7 or FIG. 8.

FIGS. 3 and 4 show a revision device according to another embodiment of the invention. As in the FIG. 2 embodiment, the caudal cups of the implanted arthroplasty device have been removed and replaced with attachment devices 180 and 180' attached to the implanted caudal stems 165 and 165'. Caudal attachment rods 182 and 182' extend from attachment devices 180 and 180'. In this embodiment, however, portions of the cephalad arms of the implanted arthroplasty device have been removed, e.g., to provide access to otherwise inaccessible portions of the spinal anatomy. Removal of such portions (or other components of the arthroplasty device) may be desirous to allow surgical access to selected anatomy (such as the intervertebral disk and/or other posterior anatomy for disc replacement and/or augmentation, and/or installation of fusion cages), removal of damaged, dislodged and/or loose portions or components, as well as those portions or components that may be causing undesirable anatomical effects (i.e., impinging upon nerves or other structures). The remaining portions 121 and 121' of the cephalad arms provide attachment points for the revision device. Specifically, cephalad attachment devices 190 and 190' attach to the cephalad arm portions by, e.g., set screws 191 and 191'. Two new cephalad arms 194 and 194' are attached to the cephalad attachment devices via attachment mounts or housings 192 and 192'. The new cephalad arms 194 and 194' attach to the caudal attachment rods 182 and 182' via mounts or connector housings 196 and 196'. As in the FIG. 2 embodiment, the revision device shown in FIGS. 3 and 4 alters the biomechanics of the implanted device by substantially eliminating movement between the cephalad and caudal members and, thereby, between the adjacent vertebrae. A crossbar (such as the crossbar shown in FIG. 2, 7 or 8) may be attached to the new cephalad arms to provide additional stability for the entire construct and/or for individual components relative to the construct (such as a loose cephalad arm).

FIGS. 5 and 6 show alternative connector housings for attaching the new cephalad arm to the remaining portion of the implanted cephalad arm. In FIG. 5, as in FIG. 3, the axis of the new cephalad arm is offset with respect to the axis of the remaining portion 121' of the implanted cephalad arm. In FIG. 6, the new cephalad arm 194' is substantially uniaxial with the remaining portion 121' of the implanted cephalad arm.

FIG. 7 is an embodiment similar to that of FIG. 2 and shows an implanted spinal arthroplasty device that has been revised by a revision device. As in the FIG. 2 embodiment, the revision device alters the biomechanics of the implanted device by substantially eliminating movement between the cephalad and caudal members and between the adjacent vertebrae. The caudal cups that had been attached to inferior vertebra 14' have been removed from their stems, which remain implanted. In place of the caudal cups, attachment devices 180 and 180' are attached to the exposed portions of the caudal sterns. Caudal attachment devices, such as rods 182 and 182', extend medially from attachment devices 180 and 180'. Cephalad arms 120 and 120' are attached to the immovable caudal attachment rods via mounts 175 and 175' or other connectors or housings. Addition of the revision device therefore substantially eliminates movement between the remaining cephalad and caudal components of the implanted arthroplasty device and between vertebrae 14 and 14'. Crossbar 184 has been added between the cephalad arms for additional stability. In this embodiment, the point at which crossbar 184 attaches to cephalad arm 120 may be adjusted through the interaction of attachment screw 188 and crossbar slot 189.

Figure 8:
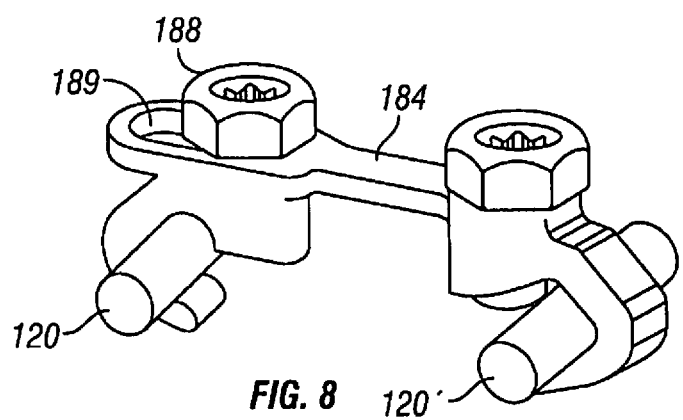
FIG. 8 shows details of a crossbar of a revision device attached to two cephalad arms.

FIG. 8 shows an alternative adjustable cephalad arm crossbar 184 for use in a spinal arthroplasty revision device. The effective length of crossbar 184 can be adjusted through the interaction of adjustment screw 188 and crossbar slot 189.

Figure 9:
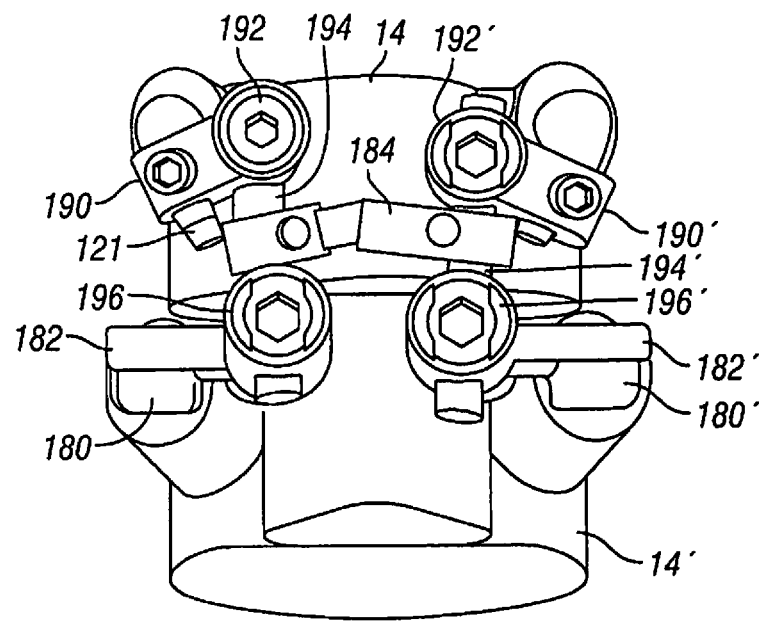
FIG. 9 shows an implanted spinal arthroplasty device that has been revised by a revision device according to yet another embodiment of the invention.

FIG. 9 shows yet another embodiment of a revision device attached to remaining portions 121 and 121' of removed cephalad arms of an implanted spinal arthroplasty device. As in other embodiments, the caudal cups of the implanted arthroplasty device have been removed and replaced with attachment devices 180 and 180' attached to the implanted caudal stems, and caudal attachment rods 182 and 182' extend from attachment devices 180 and 180'. As in the FIG. 3 embodiment, portions of the cephalad arms of the implanted arthroplasty device have been removed, e.g., to provide access to otherwise inaccessible portions of the spinal anatomy, and the remaining portions 121 and 121' of the cephalad arms provide attachment points for the revision device. Cephalad attachment devices 190 and 190' attach to the cephalad arm portions by, e.g., set screws 191 and 191'. Two new cephalad arms 194 and 194' are attached to the cephalad attachment devices via attachment mounts or housings 192 and 192'. Unlike the FIG. 3 embodiment in which the new cephalad arms are disposed lateral to the remaining portions of the implanted cephalad arms, in this embodiment the new cephalad arms 194 and 194' are medial to the remaining portions 121 and 121' of the implanted cephalad arms. Also, the new cephalad arms 194 and 194' attach to the caudal attachment rods 182 and 182' via mounts or connector housings 196 and 196' at locations medial to caudal attachment devices 180 and 180'. A crossbar 184 is attached to the new cephalad arms to provide additional stability. The revision device shown in FIG. 9 alters the biomechanics of the implanted device by substantially eliminating movement between the cephalad and caudal members and, thereby, between the adjacent vertebrae.

Figure 10:
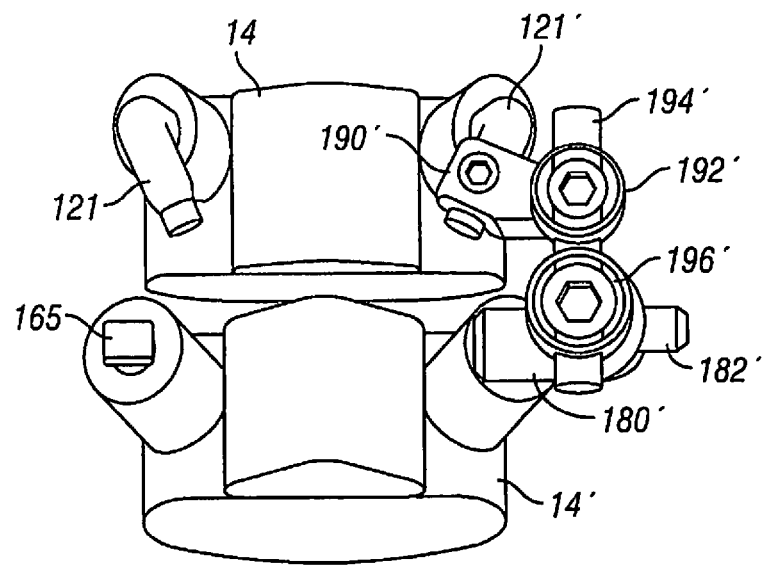
FIG. 10 shows an implanted spinal arthroplasty device that has been revised by a revision device according to still another embodiment of the invention.

FIG. 10 shows still another embodiment of a spinal arthroplasty revision device (including cephalad attachment device 190', new cephalad arm 194' and attachment housings 192' and 196') attached to only one side of the spine and lateral to both the implanted cephalad arm 121' and the caudal attachment device 180'. The remaining portion 121 of the other implanted cephalad arm and the other caudal stem 165 are not being used as part of the revision (although such portions could be utilized for the revision, if desired, or as anchoring points for other spinal hardware). Use of a lateral location for the revision device may be useful in cases where the patient's anatomy does not permit a medial position for the revision device due, e.g., to the size of the patient or to the limited amount of bone that had previously been removed and/or the location of the spinal cord/nerves and other anatomical structures.

Figure 11A:
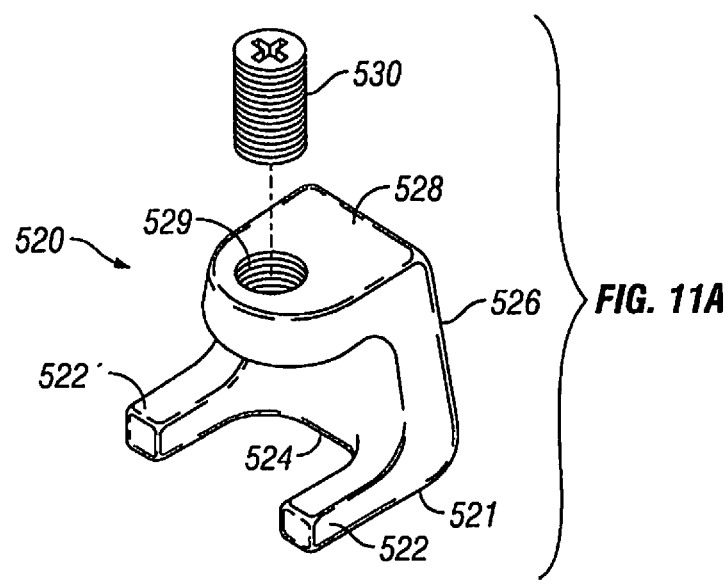
FIG. 11A illustrates a securing device for use in connection with an arthroplasty device to revise and/or modify, control, or limit motion of the arthroplasty device.

FIG. 11A illustrates a revision or securing device for use in connection with an arthroplasty device to revise and/or modify, control, or limit motion of the arthroplasty device. The securing device has a body 520 with a distal surface 521 having pair of prongs 522, 522'. When installed, the prongs 522, 522' form a base and are positioned below the crossbar member and the indenture 524 of the securing device engages the anchors on three sides. When used with a device of FIG. 1, the prongs can be positioned below the caudal cup which receives an end of the crossbar member, while the top sits above the crossbar end (110, 115) to secure the end in place within the caudal cup 150.

Figure 11B:
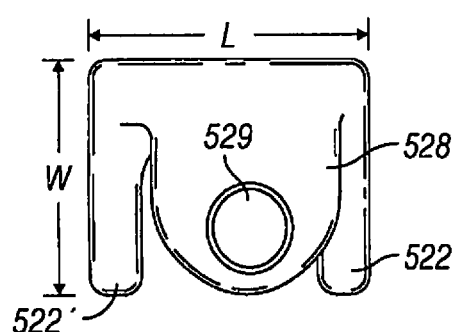
FIG. 11B is a top view of the securing device of FIG. 11A.
Figure 11C:
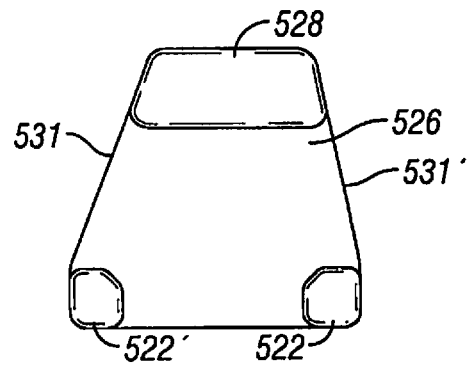
FIG. 11C is a side view of the securing device of FIG. 11A.
Figure 11D:
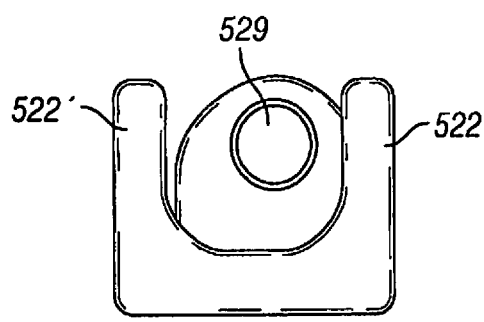
FIG. 11D is a bottom view of the securing device of FIG. 11A.
Figure 11E:
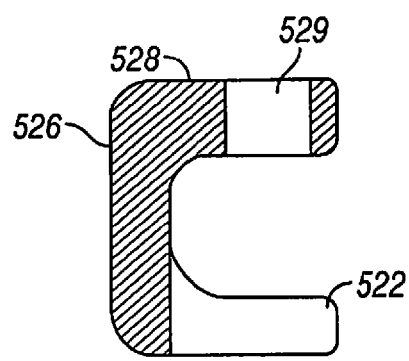
FIG. 11E is a cross-sectional view of the securing device of FIG. 11A.

The prongs 522, 522' engage a wall 526 of the securing device on one side. The wall 526 mates with a top or roof 528 that fits above the cross-bar member. The top 528 has an aperture 529. The aperture 529 can function as a detent, catch or plunger to snap fit over the ball end 110 of the crossbar member in an arthroplasty device. Alternatively, the securing device can be a securing mechanism, such as a set screw 530. FIG. 11B is a top view of the securing device 520. From this perspective, it is apparent that the top 528 can be positioned off a central axis of the device to the two prongs 522, 522', thus also potentially positioning the aperture 529 off the central axis as well. FIG. 11C is a side view of the securing device, illustrating the angled configurations of the sides 531, 531' back wall 526. The angled configuration positions the top 528, which can have a smaller dimension in at least one direction (e.g., length or width) than the length or width formed by the prongs and the wall. FIG. 11D is a bottom view of the securing device 520. FIG. 11E is a cross-sectional view of the securing device taken through an axis parallel to the prongs 522, 522'.

Figure 12A:
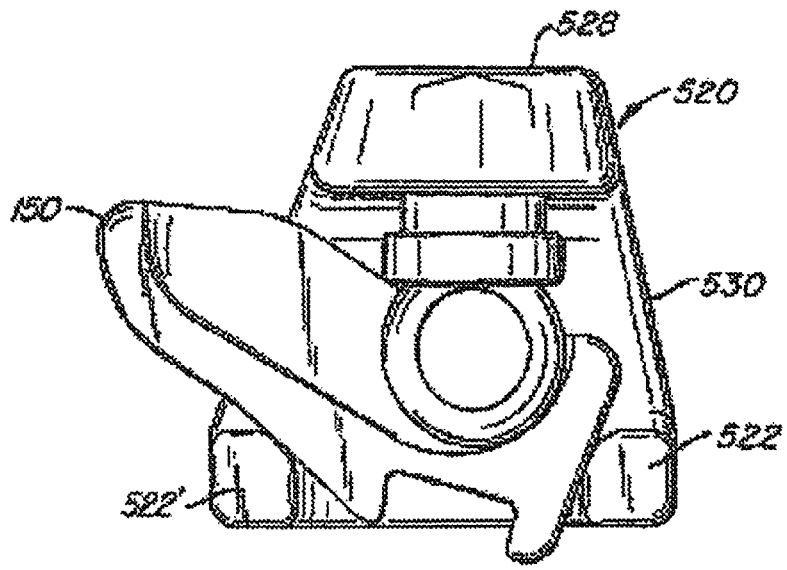
FIG. 12A illustrates a side view of the securing device of FIG. 11 in combination with a portion of the arthroplasty device of FIG. 1.
Figure 12B:
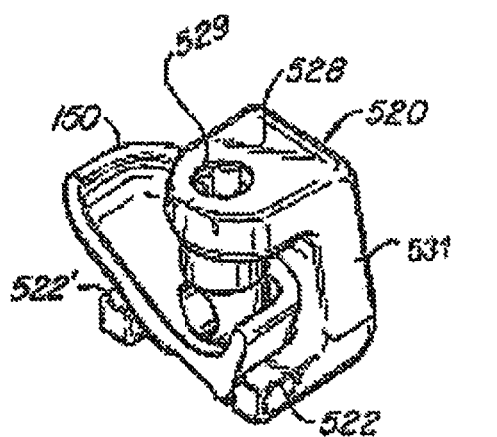
FIG. 12B illustrates a perspective view of the securing device in combination with a portion of the arthroplasty device.
Figure 12C:
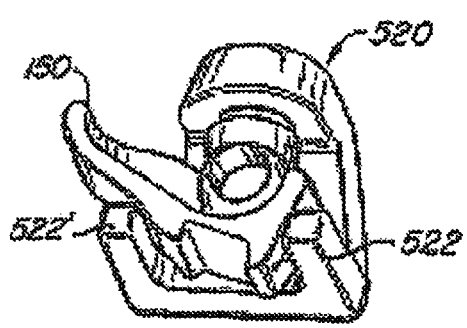
FIG. 12C is a perspective view from an anterior perspective of the securing device in combination with a portion of the arthroplasty device.
Figure 12D:
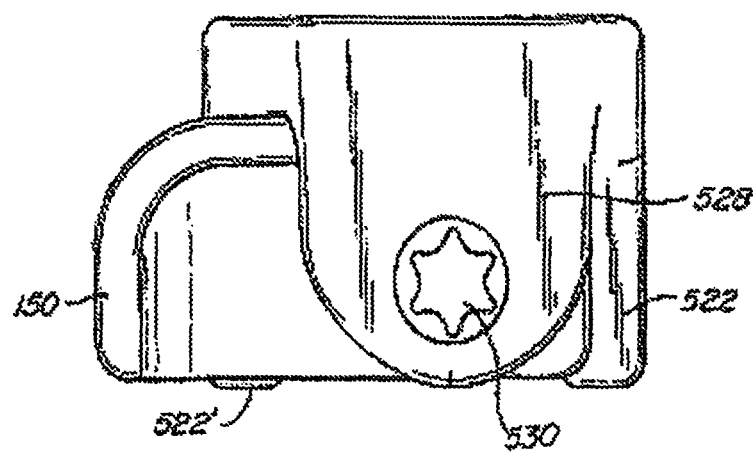
FIG. 12D is a top view of the securing device with a portion of the arthroplasty device
Figure 12E:
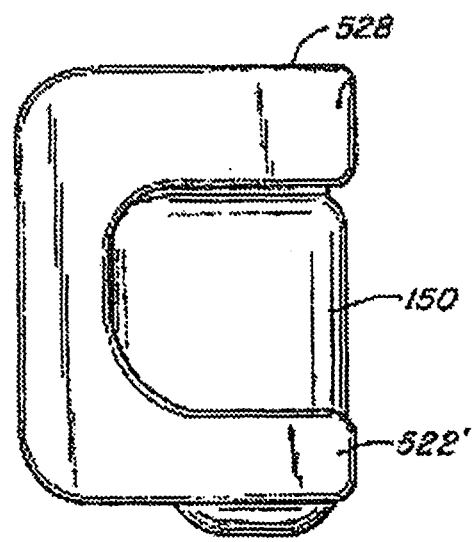
FIG. 12E is a bottom view of the securing device with a portion of the arthroplasty device.

FIG. 12A illustrates a side view of the securing device of FIG. 11 in combination with a portion of an arthroplasty device, such as the arthroplasty device of FIG. 1. The prongs 522, 522' sit below the caudal cup 150, holding the caudal cup in a fixed position. The top 528 of the securing device 520 sits above an end of the cross-member 110, which fits within the caudal cup 150. An anchoring device 530 (see FIG. 11A) can be fed through the aperture to engage the end of the cross-member and hold it in position within the caudal cup 150. As illustrated, the caudal cup 150 is tilted t toward an axial plane 52, enabling the caudal cup to secure the cross-member at a location. Adjustment of the position of the caudal cup relative to the cross-member end can affect the position of the device. FIG. 12B illustrates a perspective view of the securing device in combination with a portion of the arthroplasty device. From this perspective, a set screw 530 located within the aperture 529 on the top of the securing device can be seen. FIG. 12C is a perspective view from a partially anterior view of the securing device again in combination with a portion of the arthroplasty device. FIG. 12D is a top view of the securing device 520 with a portion of the arthroplasty device. As evident from this perspective, the caudal cup extends on one side past the prong 522'. The set screw 530 is positioned off-center relative to the length of the securing device, but the top of the securing device is positioned over the end of the cross-member. FIG. 12E is a bottom view of the securing device engaging an arthroplasty device. From this view, it is illustrated that the prongs 522, 522' are seated beneath, for example, the caudal cup of the arthroplasty device.

Thus, the implanted arthroplasty device can be revised to incorporate locks or "fusion caps" that desirably convert the device from an articulating joint replacement construct to a non-articulating (or controlled and/or limited articulation) spinal fusion construct. In this embodiment, the fusion cap can be installed on or into the caudal cups to desirably immobilize the cephalad bearings within the cups. In various embodiments, the fusion caps could immobilize the cephalad bearings by direct compression or contact, through use of a set screw or other device to secure the cephalad bearing relative to the cup, or the fusion cap could contain or cover an encapsulating material, such as bone cement, which could fill the caudal cup and immobilize the cephalad bearing. Various techniques could be used in conjunction with the installation of such fusion caps, and the cap could be installed prior to, during, or after the completion of a concurrent spinal fusion procedure, including the removal of intervertebral disc material, installation of fusion cages, and/or introduction of material (such as bone graft material) that desirably promotes spinal fusion. If desired, the bearing surface could be textured and/or knurled to increase friction between the ball, bearing surface and/or the fusion construct. Alternative embodiments could incorporate bearings of different shapes or sizes (not shown), including square or non-spherical bearings and/or bearings shaped to that fit snugly into and accommodate most or all of the interior of the caudal cup (not shown), that can be secured within the cup in a similar manner.

Figure 13A:
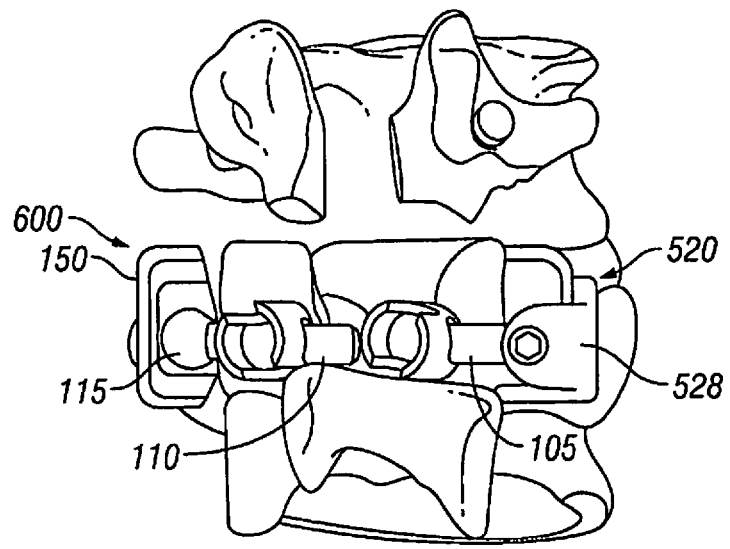
FIG. 13A is a perspective view of an implanted arthroplasty device with the securing device of FIG. 11.
Figure 13B:
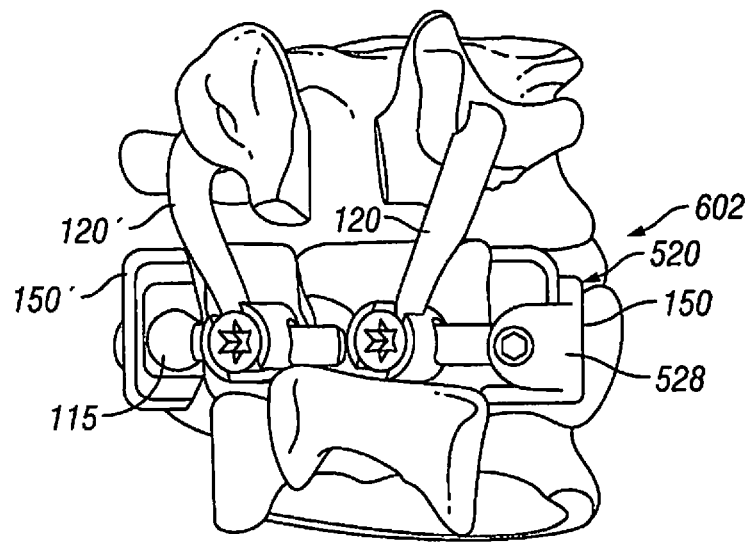
FIG. 13B is a perspective view of another implanted arthroplasty device with the securing device of FIG. 11.
Figure 13C:
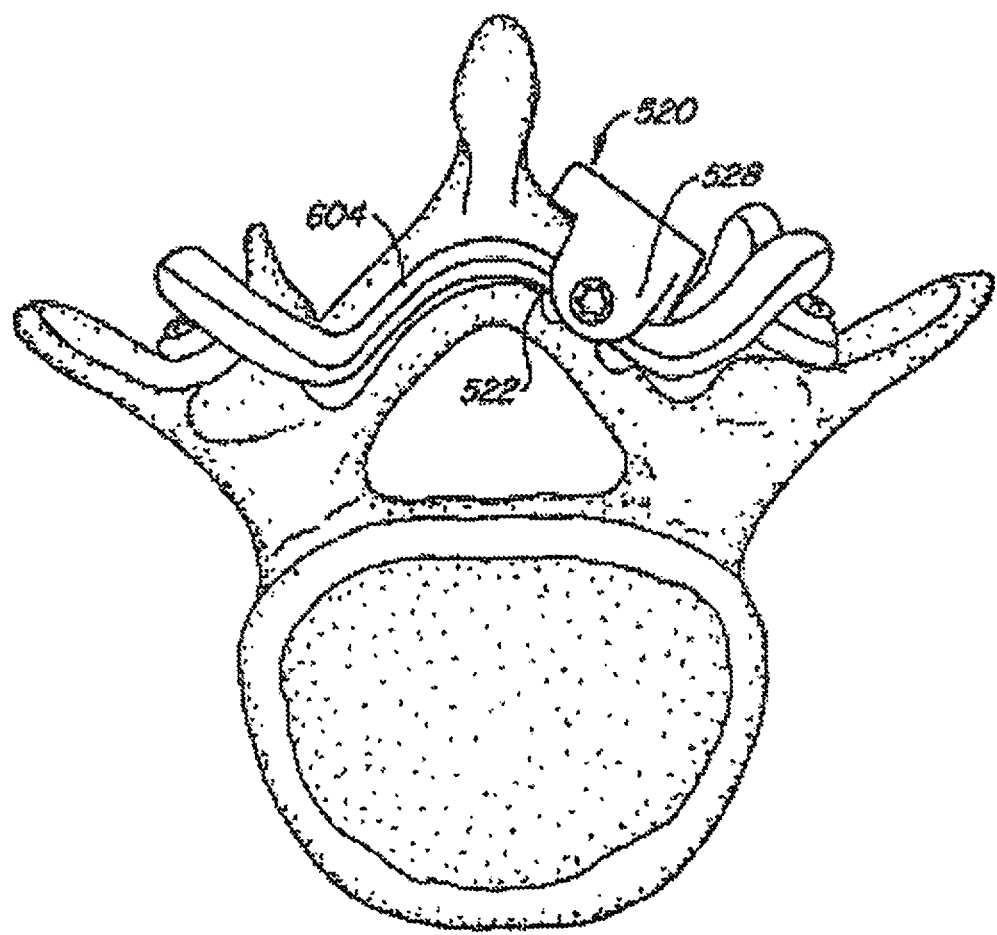
FIG. 13C is a perspective view of yet another implanted arthroplasty device with another embodiment of a securing device constructed in accordance with the teachings of the present invention.

Turning now to FIG. 13A, a perspective view of an implanted arthroplasty device 600 with the securing device of FIG. 11 is illustrated. The arthroplasty device 600 features a pair of caudal cups 150 engaging a cross-member 110. The cephalad arms have been removed, but it has been determined desirable to keep the caudal cups and cross-bar in place. The use of the securing device enables the caudal cup and crossbar member to be retained in position even without one or more of the cephalad arms to anchor the cross-member. Additionally, as will be appreciated by those of skill in the art, one of the two cephalad arms could be removed with the use of one or two of the securing devices to provide a three-point secured device (i.e., rigidly connecting two caudal cups to a single cephalad arm). The securing device engages the caudal cup and an end of the cross-member in the manner described above. FIG. 13B is a perspective view of another implanted spinal arthroplasty device 602 having a pair of caudal cups 150, 150' engaging a cross-member 110 and a pair of cephalad arms 120, 120' extending vertically toward the adjacent vertebra 12 along with the securing device of FIG. 11. FIG. 13C is a perspective view of yet another implanted arthroplasty device 604 with the securing device of FIG. 11.

Figure 14:
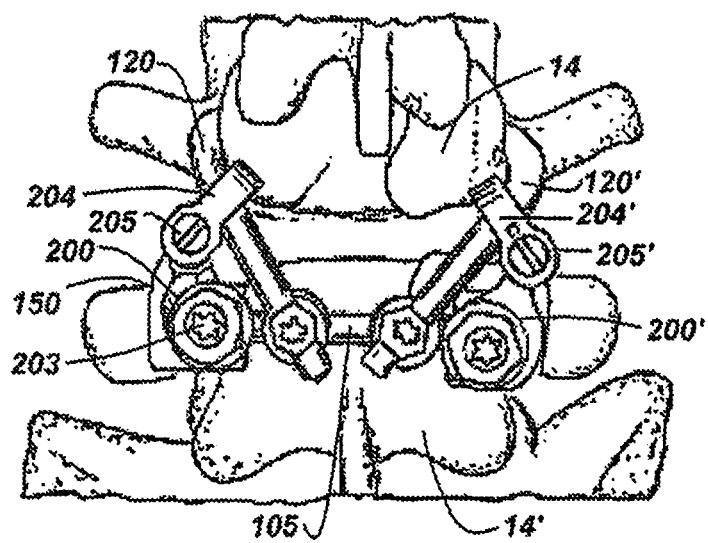
FIG. 14 shows an implanted spinal arthroplasty device that has been revised by a revision device according to another embodiment of the invention.
Figure 15:
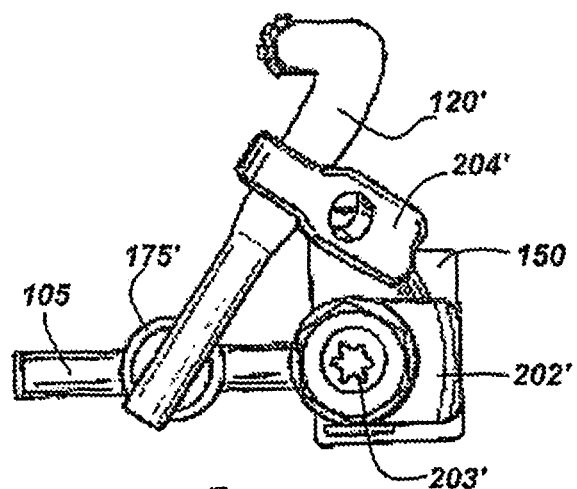
FIG. 15 shows a top view of certain components of the revision device and implanted arthroplasty device of FIG. 14.
Figure 16:
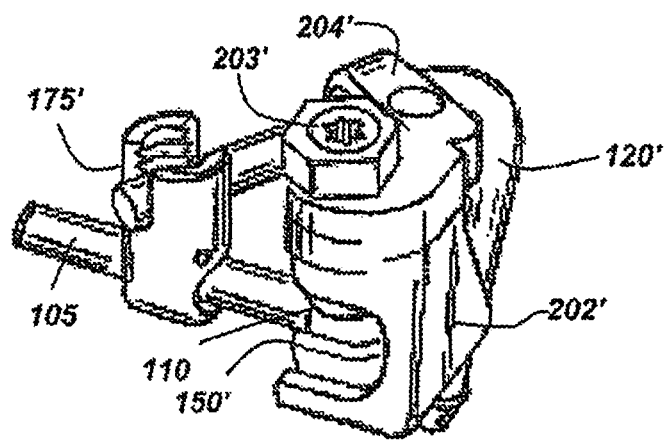
FIG. 16 shows a perspective view of certain components of the revision device and implanted arthroplasty device of FIG. 14.
Figure 17:
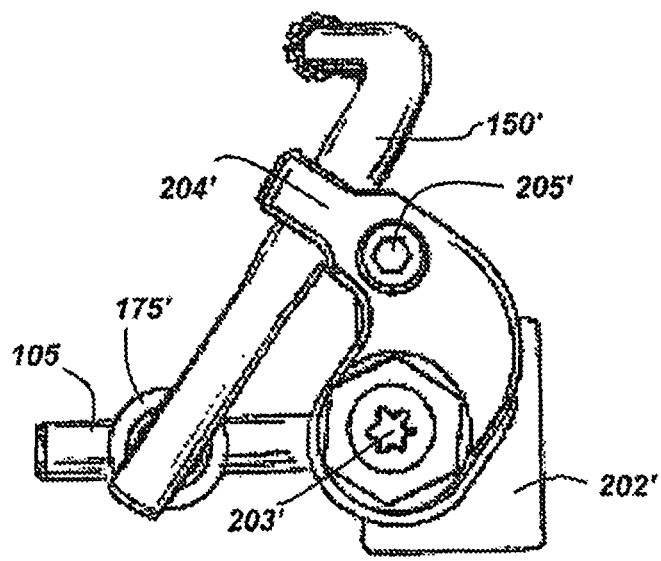
FIG. 17 shows a top view of certain components of an alternative revision device and implanted arthroplasty device.
Figure 18:
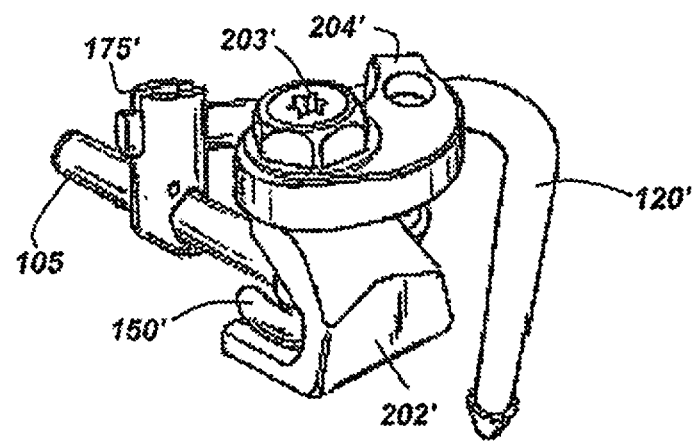
FIG. 18 shows a perspective view of the components of the revision device and implanted arthroplasty device of FIG. 17.

FIGS. 14-18 show still other embodiments of a spinal arthroplasty revision system according to the invention. FIGS. 14-16 show an implanted spinal arthroplasty system (such as that shown in FIG. 1) with cephalad arms 120 and 120', cephalad heads (such as head 110 shown in FIG. 16) at either end of a cephalad crossbar 105 and caudal cups 150 and 150'. The cephalad arms connect to crossbar 105 via crossbar mounts 175 and 175'. Revision devices 200 and 200' have been added to the implanted arthroplasty prosthesis to substantially eliminate movement between the cephalad heads and the caudal cups and, thereby, between adjacent vertebrae 14 and 14'. As shown in detail in FIGS. 15 and 16, the revision device includes a securing section 202' similar to that of FIG. 11 extending from one side of the caudal cup 150' to an opposing side of the cephalad head 110. Securing sections 202 and 202' lock the cephalad heads against the caudal cups with screws and 203 and 203'. Cephalad arm hook plates and connectors 204 and 204' are attached to the securing section 202' (via screw 203 or 203') and to cephalad arms 120 and 120' (via set screw 205 or 205') to provide additional stability. The upper surfaces of the securing sections 202 and 202's and the lower surfaces of hook plates 204 and 204' may have complementary shapes (e.g., spherical) and roughened surface texture to form a more secure connection between them. Revision devices 200 and 200' alter the biomechanics of the implanted device by substantially eliminating movement between the cephalad and caudal members and between the adjacent vertebrae, thereby transforming the implanted spinal arthroplasty device into a fusion device.

FIGS. 17 and 18 show an alternative design to the revision devices 200 or 200' of FIGS. 14-16. 100671 The first step of adding a revision system, such as one of those shown above in FIGS. 14-18, to an implanted spinal arthroplasty device, is to expose the existing device. Bone and/or soft tissue may be removed from under the caudal cup to make room for the securing device, such as securing device 202 or 202' in FIGS. 14-18. After placing the securing devices 202 and 202' around caudal cups 150 and 150' and the cephalad heads at either end of crossbar 105, screws 203 and 203' are tightened (to, e.g., 70 in-lbf) to hold the cephalad and caudal components together. The cephalad heads are preferably in the "home" position within their respective caudal cups. The vertebrae can be compressed prior to final assembly of the revision device, if desired. A hook plate of suitable size and dimensions is selected (from, e.g., a kit containing multiple hook plates of various sizes) and placed over a portion of the securing device screw 203 or 203' extending above the securing device 202 or 202'. The hook plate is attached to its corresponding cephalad arm via set screw 205 or 205'. Bone graft material may be added to facilitate fusion. The incision may then be irrigated and closed in a standard fashion.

The revision devices of this invention may be provided in kits containing components of various sizes so that the revision device can be tailored to the patient's anatomy. In addition, the kits may contain the removal, sizing and implantation tools needed to perform the revision procedure.

Figure 19:
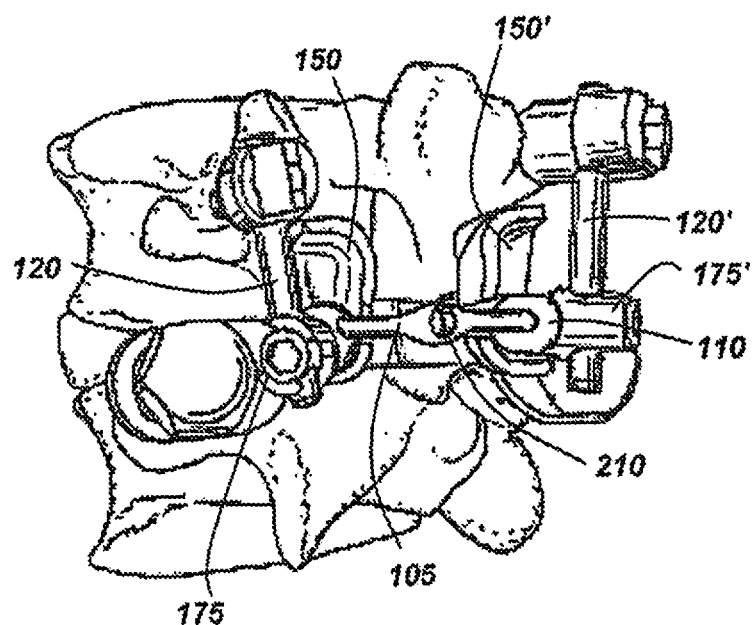
FIG. 19 shows an implanted spinal arthroplasty device with attachment holes for a revision device

FIG. 19 shows an implanted spinal arthroplasty device similar to that shown in FIG. 1. As in the FIG. 1 embodiment, cephalad arms 120 and 120' connect via crossbar mounts 175 and 175' to a cephalad crossbar 105 having heads 110 and 115 at either end. In this device, however, the caudal cups 150 and 150' are connected with a crossbar 212 as well. In addition, cephalad crossbar 105 has an opening 210 that lines up with an opening (not shown) in caudal crossbar 212. The two openings may be used to secure a revision device, e.g., to secure the cephalad and caudal components together during installation or to limit or eliminate the range of motion between the cephalad and caudal components.

While the various embodiments of the invention have been described in the context of a spinal arthroplasty device revision that substantially eliminates motion between the cephalad and caudal device components (i.e., fusion), it should be understood that the revision device may alter but still permit motion between the cephalad and caudal components.

What is claimed is:

1. A system for implantation comprising:
   a first caudal cup having a first bearing surface;
   a second caudal cup having a second bearing surface;
   a crossbar member extending between the first caudal cup and the second caudal cup, wherein the crossbar member has a first end that engages the first bearing surface of the first caudal cup and has a second end that engages the second bearing surface of the second caudal cup; and
   a securing device for limiting motion of the system, the securing device including a lower portion and an upper portion, wherein the lower portion is disposed in a position anterior relative to the first caudal cup and the lower portion is configured to receive the first caudal cup between a pair of prongs, and wherein the upper portion is configured to engage the first end of the crossbar member at a position opposing the first bearing surface of the first caudal cup.

2. The system of claim 1, wherein the first end of the crossbar member comprises a head member.

3. The system of claim 1, wherein the pair of prongs comprises a first prong and a second prong opposing one another at the lower portion.

4. The system of claim 3, wherein the first prong and the second prong straddle a portion of the first caudal cup.

5. The system of claim 1, wherein the upper portion of the securing device comprises a roof with an aperture therethrough.

6. The system of claim 5, wherein the roof receives a set screw that engages the first end of the crossbar member.

7. The system of claim 1, wherein the upper portion of the securing device comprises a roof having a set screw received therein, wherein the set screw is off-center relative to an overall length of the securing device.

8. The system of claim 1, wherein the securing device comprises a three-point securing device around the first caudal cup and the crossbar member.

9. A system for implantation comprising:
a first caudal cup having a first bearing surface;
a second caudal cup having a second bearing surface;
a crossbar member extending between the first caudal cup and the second caudal cup, wherein the crossbar member has a first end that engages the first bearing surface of the first caudal cup and has a second end that engages the second bearing surface of the second caudal cup; and
a securing device for limiting motion of the system, wherein the securing device comprises a three-point securing device around the first caudal cup and the crossbar member, wherein the lower portion of the securing device is disposed anterior relative to the first caudal cup and the lower portion is configured to receive the first caudal cup between a pair of prongs, and wherein an upper portion of the securing device is configured to engage the first end of the crossbar member at a position opposing the first bearing surface of the first caudal cup.

10. The system of claim 9, wherein the pair of prongs comprises a first prong and a second prong opposing one another at the lower portion of the securing device.

11. The system of claim 10, wherein the securing device further comprises a roof.

12. The system of claim 11, wherein the roof comprises an aperture therein.

13. The system of claim 12, wherein the roof receives a set screw through the aperture.

14. The system of claim 13, wherein the set screw engages the crossbar member and the first prong and the second prong engage the first caudal cup.

15. The system of claim 13, wherein the set screw is off-center from a central axis of the securing device.

16. The system of claim 9, wherein the first end and the second end of the crossbar member comprise rounded ends.

17. A securing device for implantation, comprising:
an upper portion comprising a roof;
a lower portion comprising a first prong and a second prong, wherein the lower portion is configured to be disposed in a position anterior to a first caudal cup and to receive the first caudal cup between the first prong and the second prong; and
a surface extending between the upper portion and the lower portion,
wherein the roof is offset from a central line that extends between the first prong and the second prong.

18. The securing device of claim 17, wherein the roof comprises an aperture extending therethrough.

19. The securing device of claim 18, further comprising a set screw received in the aperture.

20. The securing device of claim 19, wherein the set screw is threaded.

* * * * *